United States Patent [19]

Anderson

[11] Plant 4,075

[45] July 12, 1977

[54] DWARF PEACH TREE

[75] Inventor: Frederic W. Anderson, Merced, Calif.

[73] Assignee: Stribling's Nurseries, Inc., Merced, Calif.

[21] Appl. No.: 712,843

[22] Filed: Aug. 9, 1976

[51] Int. Cl.[2] ..... A01H 5/03

[52] U.S. Cl. ..... Plt./43

[58] Field of Search ..... Plt./43

*Primary Examiner*—Robert E. Bagwill

*Attorney, Agent, or Firm*—Roger B. Webster

[57] ABSTRACT

A genetically dwarf peach tree which is medium size, vigorous, spreading, foliated with large, lanceolate, acutely pointed leaves having a crenate margin, blooms with large pink flowers, and is a regular and productive bearer of large to medium size, uniform, symmetrical freestone fruit having yellow skin overspread to a substantial extent with red, yellow flesh, and a beige stone.

1 Drawing Figure

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of dwarf peach tree resulted from my endeavors in the conduct of such plant breeding program.

ORIGIN OF THE VARIETY

The present variety of genetically dwarf peach tree was originated by me, in my experimental nursery and orchard located as aforesaid, as an open-pollinated seedling of the "Empress" dwarf peach tree (U.S. Plant Pat. No. 2,533). The variety, as thus originated, and under careful and continuing observation, evidenced — upon bearing fruit — certain novel characteristics which were commercially desirable, and I, therefore, undertook asexual reproduction of the variety preparatory to introducing it to the trade.

ASEXUAL REPRODUCTION OF THE VARIETY

Subsequent to origination and selection by me of the present variety of peach tree, in the manner above described, I asexually reproduced it by top-working on mature trees in my said experimental orchard, and — in maturity — such reproductions ran true to the original tree in all respects.

SUMMARY OF THE VARIETY

The herein claimed new and distinct variety of genetically dwarf peach tree is medium size, vigorous, spreading, foliated with large, lanceolate, acutely pointed leaves having a crenate margin, blooms with large pink flowers, and is a regular and productive bearer of large to medium size, uniform, symmetrical freestone fruit having yellow skin overspread to a substantial extent with red, yellow flesh, and a beige stone; the variety having the general characteristics of the Empress, the seed parent, but is distinctive, in comparison, by fruit which is of better eating quality and ripens about 3 weeks earlier.

BRIEF DESCRIPTION OF THE DRAWING

The drawing is an illustration, by photographic reproduction in color, of leaves and fruit of the variety; one of the fruit being cut into halves to expose the flesh, with the stone remaining in one such half.

DESCRIPTION OF THE VARIETY

The botanical details of this new and distinct variety of dwarf peach tree — with color definitions (except those in common color terms) referenced to Maerz and Paul Dictionary of Color — are as follows:

Tree:
- *Class.*—Genetically dwarf.
- *Size.*—Medium, as compared to other dwarf peach trees.
- *Vigor.*—Vigorous.
- *Growth.*—Spreading.
- *Production.*—Productive.
- *Bearing.*—Regular bearer.

Trunk:
- *Size.*—Medium.

Branches:
- *Size.*—Stocky.

Leaves:
- *Size.*—Large; average length — 8¼"; average width — 1½".
- *Form.*—Lanceolate; acutely pointed.
- *Thickness.*—Medium.
- *Margin.*—Glandular; crenate.
- *Petiole.*—Medium length — average ½".
- *Glands.*—Average number and position — 2 on petiole and 2 on blade; alternate; medium size; reniform.
- *Color.*—Top side — Medium green (23-L-8); Under side — Lighter green (22-L-7).

Flower buds:
- *Size.*—Medium.

Flowers:
- *Blooming Period.*—March 3rd–March 15th, 1976; medium, as compared with other varieties.
- *Size.*—Large.
- *Color.*—Pink.

Fruit:

*Maturity When Described.*—Eating ripe.

*Date of First Picking.*—June 10th, 1976.

*Date of Last Picking.*—June 25th, 1976.

*Size.*—Large to medium; uniform; average diameter axially — 2 7/16"; average transversely in suture plane — 2½".

*Form.*—Uniform; symmetrical; globose.

*Suture.*—Shallow; extends from base to apex, with slight depression beyond pistil point.

*Cavity.*—Circular.

*Base.*—Rounded.

*Apex.*—Short.

Skin:

*Thickness.*—Medium to thin.

*Tendency to Crack.*—None noted.

*Down.*—Moderate; medium length.

*Color.*—Yellow (9-L-4) overspread to a substantial extent with red (5-K-5).

Flesh:

*Texture.*—Medium; fine; melting.

*Ripens.*—Evenly.

*Aroma.*—Distinct.

*Eating Quality.*—Good to best.

*Color.*—Yellow (9-L-5).

*Surface of Pit Cavity.*—Yellow (9-L-4).

Stone:

*Type.*—Free.

*Size.*—Medium; average length — 1½"; average breadth — 1¼"; average thickness — ⅝".

*Form.*—Obovoid.

*Sides.*—Equal.

*Tendency to Split.*—None noted.

*Color.*—Beige (11-H-7).

Use: Market — local.

Keeping quality: Medium.

Resistance to insects and diseases: No unusual susceptibilities noted; few culls.

Shipping Quality: Medium.

The dwarf peach tree and its fruit herein described may vary in slight detail due to climatic and soil conditions under which the variety may be grown; the present description being of the variety as grown in the Central Valley of California.

I claim:

1. A new and distinct variety of genetically dwarf peach tree, substantially as shown and described, which is of medium size, vigorous, spreading, foliated with large, lanceolate, acutely pointed leaves having a crenate margin, blooms with large pink flowers, and is a regular and productive bearer of large to medium size, uniform, symmetrical freestone fruit having yellow skin overspread to a substantial extent with red, yellow flesh, and a beige stone; the variety having the general characteristics of the Empress, the seed parent, but is distinctive, in comparison, by fruit which is of better eating quality and ripens about 3 weeks earlier.

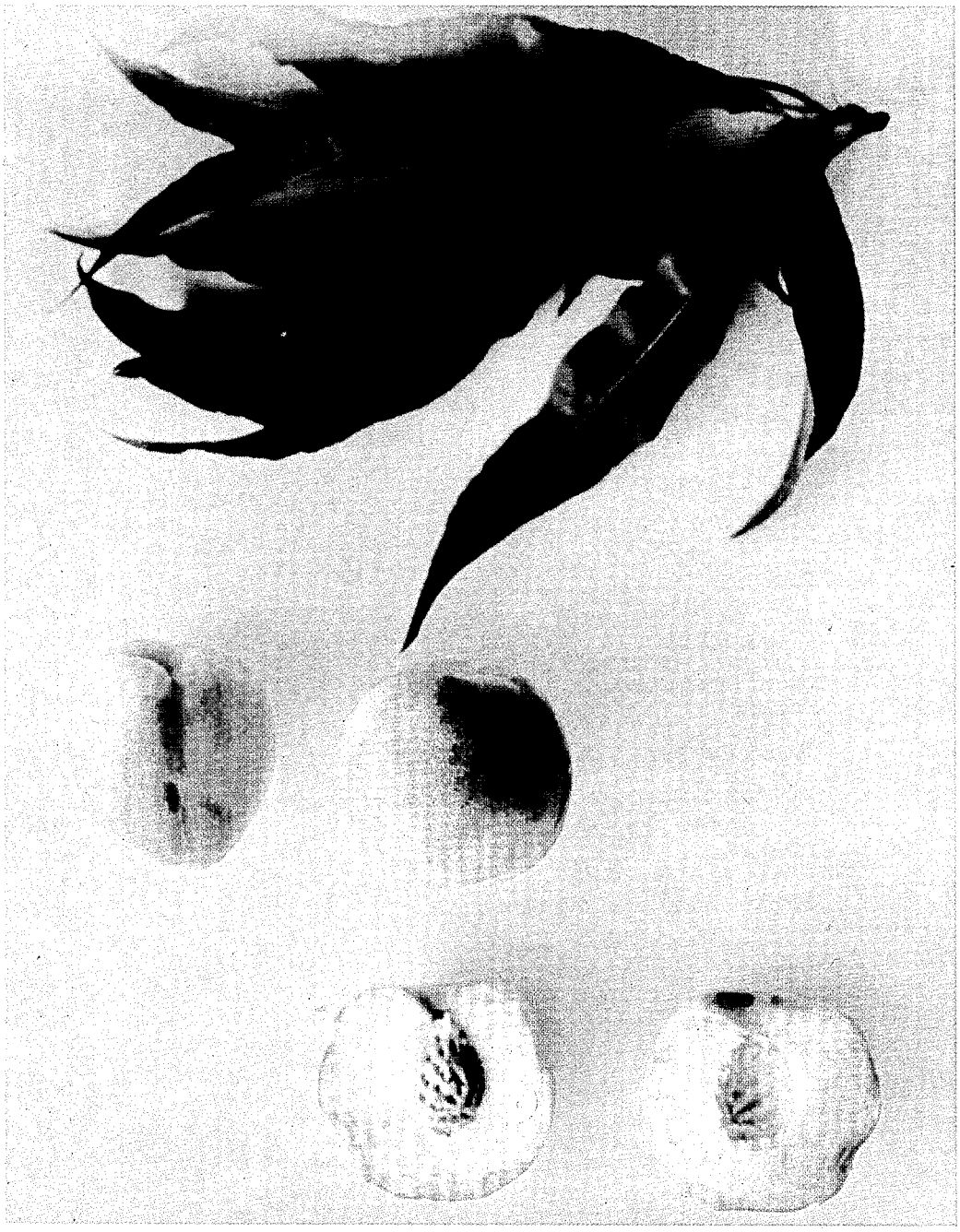

* * * * *